United States Patent
Tsuzuki et al.

(10) Patent No.: US 7,267,982 B2
(45) Date of Patent: *Sep. 11, 2007

(54) CARRIER FOR CELL CULTURE

(75) Inventors: Hirohiko Tsuzuki, Minami-ashigara (JP); Kazuhiro Aikawa, Minami-ashigara (JP); Makoto Kato, Minami-ashigara (JP); Akiko Matsuura, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 247 days.

This patent is subject to a terminal disclaimer.

(21) Appl. No.: 10/612,955

(22) Filed: Jul. 7, 2003

(65) Prior Publication Data

US 2004/0072338 A1  Apr. 15, 2004

(30) Foreign Application Priority Data

Jul. 5, 2002 (JP) ............................. 2000-196725
Jul. 5, 2002 (JP) ............................. 2000-196726

(51) Int. Cl.
*C12N 5/00* (2006.01)
(52) U.S. Cl. ..................................................... 435/401
(58) Field of Classification Search ................ 435/401, 435/397, 93.7, 198
See application file for complete search history.

(56) References Cited

U.S. PATENT DOCUMENTS 5,512,474 A * 4/1996 Clapper et al. ............. 435/402
6,821,107 B1 * 11/2004 Hara et al. .................. 435/397

FOREIGN PATENT DOCUMENTS

JP 2001-120267 5/2001
JP 3261456 12/2001

OTHER PUBLICATIONS

Huguet ML and Dellacherie E. "Calcium alginate beads coated with chitosan: effect of the structure of encapsulated materials on their release". 1996, 31(8): 745-751: entire document.*

* cited by examiner

*Primary Examiner*—Sandra E. Saucier
*Assistant Examiner*—Satyendra K. Singh
(74) *Attorney, Agent, or Firm*—Sughrue Mion, PLLC

(57) ABSTRACT

A carrier for cell culture comprising a carrier having a cationic group and polypeptide-modified portions formed on a surface of the carrier in a sea-island structure, and a carrier for cell culture comprising a water-containing gel comprising alginic acid, wherein a surface of the carrier is coated with collagen, and wherein the collagen is bound to a surface of the water-containing gel by means of chitosan.

7 Claims, 2 Drawing Sheets

←1.5mm→

CARRIER FOR CELL CULTURE

TECHNICAL FIELD

The present invention relates to a carrier for cell culture which can be used for cell culture technology, cell sheet engineering and the like.

BACKGROUND ART

In recent years, various stem cells and many methods of inducing their differentiation into somatic cells have been discovered, and therefore tissue engineering has been intensively focused as a novel medical treatment that takes the place of organ transplantation. This technology aims at in vivo or in vitro construction of organs directly used for treatments of humans, and the technology has realized many techniques of expressing organ-like functions in vitro. Thus, the technology is expected to provide high throughput (HTS) cell evaluation systems that can be used for pharmacological experiments without preparation of organs, per se, and can cope with an enormous number of tests in researches for drug design, diagnosis and the like. Further, the technology is also expected as a novel technology that enables substance production unique to mammalian cells.

Analysis of human DNA nucleotide sequences by the human genome project has been almost completed, and researches in this field have been moving to post-genomic researches using that information. An example is a tailor-made medicament, which is a frequent article on recent newspaper. The researches are expected to yield enormous markets of medicaments, and support tools for drug design and medication. DNA chips and protein chips have been currently focused as such tools, and many companies including American venture business entities are in fierce competition.

However, the number of the human genes reported by the human genome project is about 30,000 to 40,000, which is not so larger compared with the number of 13,000 in fly, and there are also many homologous genes over species. Therefore, it has been becoming clear that individuality of species cannot be determined solely based on DNA. Human genetic information is used for cell construction starting from DNA via RNA to proteins in accordance with the central dogma. Transmission of the information is not one-way, but consists of a nonlinear system including many interactions and feedback systems, i.e., a so-called complex system. In life entities, there is a mechanism imparting stability and robustness thereto. For example, in the liver, a different expression system will function depending on a state of fasting, satiety, and drinking, although a gene, cells and tissues are identical. Therefore, in order to elucidate life phenomena, it is attempted to understand a life entity as a system, not merely to focus on molecular reactions, and study by simulation on the basis of boundary conditions that can be obtained by analyzing cells and organs in vivo. This new technical field is called a bio-system engineering, which has rapidly been focused.

In order to accurately understand life phenomena, it is necessary to handle systems of at least a cellular level or higher, and for this purpose, a tool is desired in which cells or tissues are arrayed while their native functions are maintained. Thus, researches for methods of constructing cell arrays have become active. Specifically, methods of controlling hydrophilicity or hydrophobicity of a surface of solid substrate such as glass substrate by using lithography are known (S. N. Bhatia et al, Biotecnol. Prog., 14, 378 (1998); Toshihiro Akaike et al., Japanese Patent Unexamined Publication (KOKAI) No. 5-176753; Otsuka et al, 30th Biomedical Polymer Symposium, Lecture Summaries, page 9 (2001); Kikuchi et al, 30th Biomedical Polymer Symposium, Lecture Summaries, page 35 (2001) and the like). However, these methods require expensive apparatuses for lithography, and also have a problem in that carriers for cell culture cannot be prepared conveniently.

A water-containing polymer gel has a structure similar to that of a living body, and has a property of expanding or shrinking depending on external conditions such as temperature, acidity, and alkalinity. Accordingly, applications in the medical field, including a use as an artificial organ or tissue such as an artificial muscle or encapsulation of a drug therein to control an amount to be released, have been attempted, as well as applications as an anchorage of cell growth in a cell culture as a gel containing various kinds of cytokines and the like.

It is known that cells are arrayed with polarity when they form a tissue in a living body. For example, hepatocytes absorb blood components from the vascular endothelial cell side, and excrete metabolites such as bile acid from the opposite side. Since this bile acid has potent cytotoxicity, cell culture by adhering the cells on an impermeable support such as glass suffers from a problem that stable long-term culture is difficult. Although it is known that the polarity of cells is expressed by stimulation given from one way to the cells, cell culture by adhering the cells on an impermeable support raises a problem that stimulation cannot be given from the adhesion side. Further, in order to perform lithography, a photosensitive solution needs to be applied beforehand. However, a substance-permeable support will cause a problem that the photosensitive solution as well as reaction products and developing/fixing solutions permeate into the support, and toxicity or stimulation is given to cultured cells due to denaturation of the support, remaining of compounds in the support or the like.

To solve these problems, a permeable collagen membrane for cell culture, MEN-01, is sold by KOKEN CO., LTD. as a cell culture material for culturing cells with different media for the both sides of the cells. However, in this cell culture material, the collagen membrane is much swelled with a medium, and thus the material is significantly distorted during the culture. Therefore, it is difficult to observe a culture state of cells. In Japanese Patent Unexamined Publication (KOKAI) No. 2001-120267, a carrier for cell culture is proposed which comprises a porous membrane together with an alginic acid gel layer and an extracellular matrix component gel layer or an extracellular matrix component sponge layer which are laminated on the porous membrane. However, this carrier for cell culture has a microfilter layer, and therefore, growth state of cells cannot be observed under an optical microscope.

DISCLOSURE OF THE INVENTION

An object of the present invention is to provide a carrier for cell culture as means for conveniently preparing a cell array. Another object of the present invention is to provide a carrier for cell culture which enables culture with different media for the both sides of cells and convenient observation of growth state of cells under an optical microscope. The inventors of the present invention conducted various studies to achieve the foregoing objects. As a result, they found that the aforementioned objects were successfully achieved by providing a carrier for cell culture employing the following constituting elements.

The present invention thus provides a carrier for cell culture comprising a carrier having a cationic group and polypeptide-modified portions formed on a surface of the carrier in a sea-island structure. According to preferred embodiments of the invention, there are provided the aforementioned carrier for cell culture, wherein the carrier having a cationic group is a polymer compound, an inorganic compound, or an organic compound; and the aforementioned carrier for cell culture, wherein the carrier having a cationic group is a polymer compound having a cationic group, or an inorganic compound or an organic compound introduced with a cationic group by surface modification. Further, according to a preferred embodiment of the invention, there is provided the aforementioned carrier for cell culture, wherein the surface of the carrier other than the polypeptide-modified portions is coated with an anionic polysaccharide.

Further, as another preferred embodiment of the aforementioned invention, there is provided the aforementioned carrier for cell culture, wherein the carrier is a water-containing gel, and as further preferred embodiments, there are provided the aforementioned carrier for cell culture, wherein the water-containing gel is a water-containing polymer gel, and the aforementioned carrier for cell culture, wherein the water-containing gel is a water-containing anionic polymer gel. In these embodiments, it is preferable to use a water-containing gel comprising a water-containing polymer gel added with chitosan or a water-containing gel comprising a water-containing anionic polymer gel adsorbed with chitosan as the carrier having a cationic group. As particularly preferred embodiments, there are provided the carrier for cell culture, wherein the carrier is a water-containing gel comprising alginic acid, and the carrier having a cationic group is formed by applying an aqueous solution of a water-soluble cationic polymer on a surface of the water-containing gel, and the carrier for cell culture, wherein the carrier is a water-containing gel comprising alginic acid, and the carrier having a cationic group is formed by immersing the water-containing gel in a solution of a water-soluble cationic polymer. In these preferred embodiments, chitosan can be most preferably used as the water-soluble cationic polymer.

As further preferred embodiments, there are provided the aforementioned carrier for cell culture, wherein the polypeptide which modifies the surface of the carrier having a cationic group is a cell-adhesive polypeptide; the aforementioned carrier for cell culture, wherein the polypeptide which modifies the surface of the carrier having a cationic group is an extracellular matrix component; and the aforementioned carrier for cell culture, wherein the polypeptide which modifies the surface of the carrier having a cationic group is a gel-like extracellular matrix component. There are also provided the aforementioned carrier for cell culture, wherein one independent polypeptide-modified portion has an area of from 50 $\mu m^2$ to 2 $mm^2$; and the aforementioned carrier for cell culture, wherein one independent polypeptide-modified portion has an area of from 100 $\mu m^2$ to 1 $mm^2$. Preferably, the polypeptide-modified portions are formed on the carrier surface by a printing method, a spotting method, and/or an ink-jet method.

From other aspects, there are provided a method for cell culture, which comprises the step of inoculating cells on the surface of the aforementioned carrier for cell culture; a method for cell culture, which comprises the step of forming a cell layer on the surface of the aforementioned carrier for cell culture; and cell culture obtained by the aforementioned cell culture methods. The aforementioned cell culture contains cell layers formed on the surfaces of the polypeptide disposed on the carrier surface in a sea-island structure. When the carrier of the aforementioned carrier for cell culture is a water-containing gel comprising alginic acid, cell culture containing substantially no water-containing gel can be obtained from the cell culture by solubilizing the water-containing gel comprising alginic acid. The present invention thus provides a method for producing a cell culture, which comprises the step of allowing cells to form a cell layer on the surface of the aforementioned carrier for cell culture, and the step of solubilizing the water-containing gel comprising alginic acid.

A further object of the present invention is to provide a carrier for cell culture which enables cell culture with a different medium for each side of cells, and convenient observation of growth state of cells under an optical microscope. The inventors of the present invention conducted various studies to achieve the foregoing objects. As a result, they found that a carrier for cell culture employing the following constituting elements had sufficient strength in a medium and enabled easy observation of cultured cells under an optical microscope. Further, they also found that this carrier for cell culture was suitably used for a cell sheet engineering. The present invention was achieved on the basis of these findings.

The present invention thus provides a carrier for cell culture comprising a water-containing gel comprising alginic acid, wherein a surface of the carrier is coated with collagen, and the collagen is bound to a surface of the water-containing gel by means of chitosan.

According to preferred embodiments of the invention, there are provided the aforementioned carrier for cell culture, wherein the water-containing gel contains calcium alginate gel or alginic acid/polylysine gel; the aforementioned carrier for cell culture, wherein the binding by means of chitosan is a bond between a collagen layer and a surface of the water-containing gel via a chitosan layer; the aforementioned carrier for cell culture, which comprises the following three laminated layers: a water-containing gel layer containing alginic acid, a chitosan layer, and a collagen layer; the aforementioned carrier for cell culture, wherein the water-containing gel layer is formed on a substrate; and the aforementioned carrier for cell culture, wherein the substrate is a porous membrane.

From other aspects, the present invention provides a method for producing the aforementioned carrier for cell culture, which comprises the step of successively immersing a water-containing gel comprising alginic acid in a chitosan solution and then in a collagen solution; and a method for producing the aforementioned carrier for cell culture, which comprises the step of successively applying a chitosan solution and then a collagen solution to a water-containing gel comprising alginic acid.

From other aspects, there are provided a method for cell culture, which comprises the step of inoculating cells on the surface of the aforementioned carrier for cell culture; a method for cell culture, which comprises the step of allowing cells to form a cell layer on the surface of the aforementioned carrier for cell culture; and cell culture obtained by the aforementioned cell culture methods. The aforementioned cell culture contains a cell layer formed on the surface of collagen which coats the water-containing gel comprising alginic acid, and cell culture containing substantially no water-containing gel can be obtained from the cell culture by solubilizing the water-containing gel comprising alginic acid. The present invention thus provides a method for producing cell culture, which comprises the step of allowing cells to form a cell layer on the surface of the aforementioned carrier for cell culture and the step of solubilizing the water-containing gel comprising alginic acid.

BEST MODE FOR CARRYING OUT THE INVENTION

Figure 1:
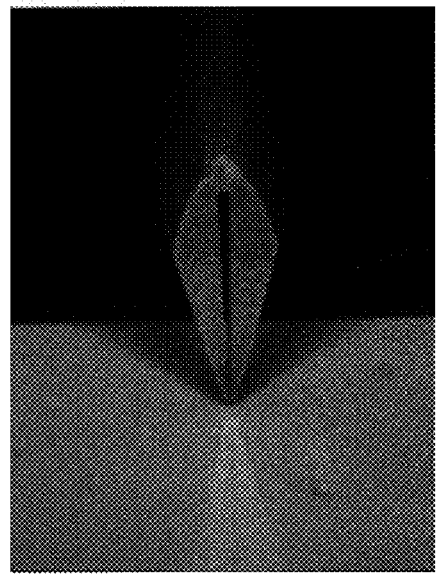
FIG. 1 shows formation of modified portions in a sea-island structure by spotting a cell-adhesive polypeptide (collagen) to a carrier surface.

The "carrier for cell culture" used in the specification means a structure that can retain cells in a culture medium during cell culture. However, this term should not be construed any limitative way, and should be construed in its broadest sense.

The carrier for cell culture of the present invention is characterized in that it comprises a carrier having a cationic group, and a surface of the carrier is modified with a polypeptide in a sea-island structure. Examples of the carrier contained in the carrier for cell culture of the present invention include carriers comprising a polymer compound, an inorganic compound, an organic compound or the like. However, the carrier is not limited to these examples. For example, a metal plate, glass or the like can also be used as the carrier. More specifically, examples of the carrier having a cationic group include, for example, those comprising a polymer compound having a cationic group, an inorganic compound or organic compound introduced with a cationic group by surface modification and the like. The cationic group is not particularly limited, so long as the group has positive charge at pH of 8 or lower. Examples include, for example, amino group; monoalkylamino group such as methylamino group and ethylamino group; dialkylamino group such as dimethylamino group and diethylamino group; imino group; guanidino group and the like.

Examples of the polymer compound having a cationic group usable as the carrier include, for example, chitosan, partially deacetylated chitin, aminated cellulose, polylysine, polyarginine, copolymer of lysine and arginine, polyvinylamine, polyaniline, polyion complexes of these compounds with anion polymers and the like. Examples of the carrier comprising an inorganic compound include glass.

When an inorganic compound or organic compound introduced with a cationic group by surface modification is used as the carrier, method for the surface modification is not particularly limited. Examples of the method include, for example, a method of using a chemical reaction to form a covalent bond, a method of achieving adsorption by electrostatic interaction of ions, a method of adhering a compound having amino group by hydrophobic interaction, a method of applying a water-insoluble amino group-containing compound and the like.

More specifically, examples of the method of using a chemical reaction to form a covalent bond include a method of using a coupling agent (silane, titanium and the like), a method of forming a self-organized membrane using a mercapto compound, a method of employing a reaction using a cationic compound having a reactive group (guanidyl, aldehyde and the like). Examples of the method of achieving adsorption by electrostatic interaction of ions include a method of allowing a multivalent cationic compound or a cationic polymer compound to adsorb on an anionic surface. Examples of the method of adhering a compound having amino group by hydrophobic interaction include a method of using an LB membrane and the like. Examples of the method of applying a water-insoluble amino group-containing compound include a method of dissolving an oil-soluble compound (alkylamine, polyaniline and the like) in an organic solvent and coating the solution, a method of applying an acid-soluble compound (chitosan and the like) as an acidic solution and then increasing pH to deposit the compound and the like. However, the method for the surface modification is not limited to these specific examples, and the method can be suitably chosen by those skilled in the art depending on the type of the carrier, the purpose of modification and the like.

A preferred embodiment of the carrier for cell culture of the present invention is, for example, the carrier for cell culture wherein the carrier is a water-containing gel, and a preferred example of the water-containing gel is a water-containing polymer gel. In the specification, the water-containing polymer gel means a substance in a form of a gel wherein a cancellous structure is formed by chemical bonds, and a large volume of water is retained in the cancellous structure. This term should not be construed any limitative way, and should be construed in its broadest sense. As the water-containing gel constituting the carrier, a water-containing gel of an inorganic substance (silica gel and the like) may also be used.

Examples of the polymer compound that forms the water-containing polymer gel include, for example, anionic polysaccharides (alginic acid, hyaluronic acid, chondroitin sulfate, dextran sulfate, agaropectin, carragheenan, carboxymethylcellulose and the like) and salts thereof, cationic polysaccharides (chitosan, partially deacetylated chitin, aminated cellulose and the like) and salts thereof, nonionic polysaccharides (dextran, cellulose, cellulose acetate, hydroxyethylcellulose, methylcellulose, agarose, amylose, glycomannan and the like), polypeptides (collagen, gelatin, silk fibroin and the like), synthetic polymers (polyacrylic acid, polyacrylamide, poly-N-isopropylacrylamide, polyethyleneimine, polyvinyl alcohol, polyethylene glycol and the like), mixtures and complexes of these substances and the like.

As the water-containing gel having a cationic group, for example, a water-containing gel of chitosan, as well as a water-containing gel comprising water-containing polymer gel added with chitosan and a water-containing gel comprising a water-containing anionic polymer gel adsorbed with chitosan can be preferably used. For example, examples include an aqueous gel prepared by dissolving chitosan with an acid and then increasing a pH so as to become water-insoluble, and an aqueous gel comprising a polyion complex of chitosan and a water-soluble anionic polymer (alginic acid, hyaluronic acid, chondroitin sulfate, dextran sulfate, agaropectin, carragheenan, carboxymethylcellulose, polyacrylic acid and acrylic acid copolymer and polymethacrylic acid and methacrylic acid copolymer, polystyrenesulfonic acid and styrenesulfonic acid copolymer and the like) or an amphoteric polymer (gelatin, collagen and the like). Examples of the method for producing the aqueous gel comprising a polyion complex include, for example, a method of mixing an aqueous solution of chitosan and an aqueous solution of an anionic or amphoteric polymer, a method of alternately immersing an aqueous gel in an aqueous solution of chitosan and an aqueous solution of an anionic or amphoteric polymer, i.e., so-called the layer-by-layer method, and the like. When the layer-by-layer method is used, it is preferable to use chitosan for the uppermost layer (final immersion solution). The aforementioned water-containing gel containing chitosan may be added with a compound not directly contributing to the gelation.

As the water-containing gel constituting the carrier, a water-containing anionic polymer gel can be used. The anionic polymer gel means an anionic polymer gelled by formation of a chelate structure with an acid radical in the molecule of the anionic polymer and a polyvalent metal ion. This term should not be construed any limitative way. Specific example of the polyvalent metal cation that can cause gelation of anionic polymer include, for example, metal ions such as barium (Ba), lead (Pb), copper (Cu), strontium (Sr), cadmium (Cd), calcium (Ca), zinc (Zn), nickel (Ni), cobalt (Co), manganese (Mn), iron (Fe) and magnesium (Mg) ions. Among them, particularly preferred are calcium ion, magnesium ion, barium ion and strontium ion. Further, the water-containing anionic polymer gel may be a water-containing gel comprising a polyion complex of an organic polymer compound having an acid radical and a cation residue. Examples of the organic polymer compound having a cation residue include compounds having two or more amino groups such as polylysine, chitosan, gelatin, and collagen.

As the carrier constituting the carrier for cell culture of the present invention, a water-containing anionic polymer gel can be preferably used, and a water-containing gel comprising alginic acid is most preferably used.

The "alginic acid gel" means alginic acid gelled by a chelate structure formed with a carboxylic acid group in the molecule of alginic acid and a polyvalent metal ion, and "alginic acid gel layer" specifically referred to in the present specification means alginic acid gel in the form of a layer.

Alginic acid is a block copolymer consisting of glucuronic acid (G) and mannuronic acid (M), and it is considered that the polyvalent metal cation enters into a pocket structure of the M block to form an egg box and thereby cause the gelation. Specific examples of the polyvalent metal cation that can cause the gelation of alginic acid include, for example, metal ions such as barium (Ba), lead (Pb), copper (Cu), strontium (Sr), cadmium (Cd), calcium (Ca), zinc (Zn), nickel (Ni), cobalt (Co), manganese (Mn), iron (Fe) and magnesium (Mg) ions. Among them, particularly preferred are calcium ion, magnesium ion, barium ion and strontium ion. The "alginic acid gel" may be a polyion complex gel of alginic acid and an organic polymer compound having a cationic residue. Examples of the organic polymer compound having a cationic residue include compounds having two or more amino groups such as polylysine, chitosan, gelatin, and collagen.

Alginic acid exists in nature as a cell wall-constituting polysaccharide or intercellular filling substance of brown algae, and can be obtained from the algae as raw materials. Examples of the brown algae as a raw material include brown algae belonging to Order Fucales, Family Durvilleaceae, Genus Durvillea (e.g., *D. potatorum*), Order Fucales, Family Fucaceae, Genus Ascophyllum (e.g., *A. nodosum*), Order Laminariales, Family Laminariaceae, Genus Laminaria (e.g., *Laminaria japonica, Laminaria longissima*), Order Laminariales, Family Laminariaceae, Genus Eisenia (e.g., *Eisenia bicyclis*), Order Laminariales, Family Laminariaceae, Genus Ecklonia (e.g., *Ecklonia cava, Ecklonia kurome*), and Order Laminariales, Family Lessoniaceae, Genus Lessonia (e.g., *L. flavikans*). Commercially available alginic acid can also be used. A G/M ratio of alginic acid is not particularly limited. A larger G/M ratio provides a higher gel formation ability, and accordingly, a larger G/M ratio is more preferred. Specifically, the ratio may preferably be from 0.1 to 1, more preferably from 0.2 to 0.5 (numerical ranges indicated by "(from)—to—" in the specification include lower and upper limits).

The gelation of alginic acid may be achieved in a conventional manner. For example, the gelation of alginic acid can be carried out by using ion exchange. For example, when calcium ions are added to an aqueous solution of sodium alginate, ion exchange quickly occurs to give calcium alginate gel. More specifically, a calcium alginate gel layer can be formed on a substrate by applying an aqueous solution of sodium alginate with a desired thickness on the substrate and then immersing the substrate in a solution of a polyvalent metal cation or an organic polymer compound having a cation residue.

When the aforementioned method is performed, the concentration of sodium alginate is not particularly limited. For example, a concentration of from 0.05 mass % to 20 mass % is preferred, and a concentration of from 0.5 mass % to 10 mass % or lower is particularly preferred. The thickness for coating sodium alginate is, for example, preferably from 1 μm to 100 mm, most preferably from 10 μm to 10 mm. The concentration of the solution of a polyvalent metal cation is preferably from 0.05 mol/L to 10 mol/L, most preferably from 0.1 mol/L to 5 mol/L. As the solvent of the polyvalent metal cation solution, water, a water-soluble organic solvent, and a mixture of water and a water-soluble organic solvent can be exemplified. More specifically, water, methanol, ethanol, isopropyl alcohol or a mixture thereof is preferably used, and a mixture of water and methanol is most preferably used.

When polylysine is used as the organic polymer compound having a cation residue for performing the aforementioned method, a method is preferably used in which lysine is polymerized with N-hydroxysuccinimide and 1-ethyl-3-(3-dimethylaminopropyl)carbodiimide hydrochloride in a solution of alginic acid to form polylysine. However, the method for forming an alginic acid gel or alginic acid gel layer is not limited to the aforementioned specific method. Those skilled in the art can easily produce an alginic acid gel or alginic acid gel layer by suitably altering or modifying the aforementioned method or suitably choosing other means.

When a water-containing anionic polymer gel is used as the carrier of the carrier for cell culture, the method of introducing a cationic group into the water-containing gel surface is not particularly limited. For example, a method of contacting a water-containing anionic polymer gel with a solution of water-soluble cationic polymer is preferably used. As the method for contacting with the aqueous solution, a method of applying an aqueous solution of a water-soluble cationic polymer to a surface of water-containing anionic polymer gel or a method of immersing a water-containing anionic polymer gel in an aqueous solution of a water-soluble cationic polymer is preferably used.

The carrier for cell culture according to the first embodiment of the present invention is characterized in that the surface of the carrier having a cationic group is modified with a polypeptide in a sea-island structure. As the polypeptide, a cell-adhesive polypeptide can be used. Type of cell-adhesive polypeptide is not particularly limited, so long as the polypeptide has no cytotoxicity and accepts cells adhering thereto under an ordinary culture condition, and an any natural or synthetic polypeptide can be used. Properties of the cell-adhesive polypeptide are not particularly limited. Preferably, cell-adhesive polypeptide in a gel state can be used. A most preferred example includes an extracellular matrix component gel in the form of a layer.

The extracellular matrix is generally defined as "a stable biological structure existing extracellularly in an animal tissue and is a complex aggregate formed by biological polymers which are synthesized by cells, and secreted and accumulated outside the cells" (Dictionary of Biochemistry (3rd edition), p.570, Tokyo Kagaku Dojin), and the matrix plays roles of physical support of cells, regulation of cellular activities (i.e., a role of transmitting extracellular information to a cell to change its activities) and the like. Examples of the polypeptide as the extracellular matrix component include collagen, elastin, proteoglycan, fibronectin, laminin, vitronectin, gelatin and the like. Particularly referred examples among them are collagen, atelocollagen and Matrigel (gel consisting of type IV collagen, laminin and heparan sulfate). The extracellular matrix component can be obtained in a conventional manner, and commercially available extracellular matrix components may also be used. The cell adhesion component can be gelled in a conventional manner. For example, when the cell adhesion component is collagen, a collagen gel can be obtained by incubating a 0.3 to 0.5% aqueous solution of collagen at 37° C. for from 10 to 20 minutes. A gelling agent may be used for the gelation of the extracellular matrix component, if needed.

The term "modification in a sea-island structure" used in the specification means that two or more polypeptide-modified portions exist as dots on the surface of the carrier having a cationic group, and typically means that the polypeptide-modified portions consist of discontinuous portions independent from one another. Two or more modification portions may be linked to each other or one another. The term "sea-island structure" should not be construed in any limitative way. One independent polypeptide-modified portion has an area of, for example, preferably from 50 $\mu m^2$ to 2 $mm^2$, most preferably 100 $\mu m^2$ to 1 $mm^2$. Methods for forming the polypeptide-modified portions in a sea-island structure on the surface of the carrier having a cationic group are not particularly limited. Examples of the method include, for example, methods of disposing a solution of the polypeptide on the carrier surface by a printing method (lithography, letterpress printing, intaglio printing, photogravure and the like), a spotting method utilizing a pin (capillary, tip concave mold, tip bow pen and the like), an ink-jet method and the like. However, the methods are not limited to these examples.

In the carrier for cell culture of the present invention, the areas other than the polypeptide-modified portions in a sea-island structure are preferably coated with an anionic polysaccharide. As methods for coating with an anionic polysaccharide, a method of forming polypeptide-modified portions in a sea-island structure on the carrier surface and then applying a solution of an anionic polysaccharide to the carrier surface or immersing the carrier into a solution of an anionic polysaccharide and the like may preferably be used.

The carrier for cell culture of the present invention may be formed on a substrate. When a water-containing gel is used as the carrier, the water-containing gel is preferably formed on a substrate. A porous membrane is preferably used as the substrate. The type of the porous membrane is not particularly limited. For example, those not allowing passage of the alginic acid gel but allows passage of metal ions and the like are preferably used. As the porous membrane, a membrane having small pores, as well as a membrane having voids and that having both of small pores and voids or the like may be used. Specific examples of the porous membrane include, for example, filter paper, ultrafiltration membranes, silicone rubber membranes, tetrafluoroethylene resin porous membranes (PTFE porous membranes), non-woven fabric, gauze-like mesh, various membrane filters (nylon, polyvinylidene fluoride, acetylcellulose, cellulose nitrate, polyethylene terephthalate, polycarbonate and the like), and preferred are membrane filters, in particular, membranes of nylon membrane filters. When the porous membrane has small pores, the sizes of pores are usually from 0.02 to 1,000 $\mu m$, preferably from 0.02 to 100 $\mu m$, more preferably from 0.1 to 10 $\mu m$.

The carrier for cell culture according to the second embodiment of the present invention is characterized in that the surface of the water-containing gel comprising alginic acid is coated with collagen, and the collagen is bound to the surface of water-containing gel by means of chitosan. A method of coating the surface of the water-containing gel comprising alginic acid with collagen, intermediated by chitosan, is not particularly limited. Collagen coating intermediated by chitosan can be easily formed by, for example, successively contacting the surface of the water-containing gel comprising alginic acid with an aqueous solution of chitosan and then with an aqueous solution of collagen. More specifically, the desired collagen coating can be formed by immersing the surface of the water-containing gel comprising alginic acid in an aqueous solution of chitosan, washing the gel with water, then immersing the gel in an aqueous solution of collagen and subsequently drying the gel. Further, a method of successively applying an aqueous solution of chitosan and an aqueous solution of collagen to the surface of the water-containing gel comprising alginic acid can also be employed.

When the aforementioned method is performed, a concentration of the aqueous solution of chitosan is preferably from 0.01 mass % to 10 mass %, most preferably from 0.1 mass % to 5 mass %. When the solubility of chitosan is insufficient, an acid may be added for an aid of dissolution. As the acid, acetic acid, hydrochloric acid, phosphoric acid and the like can be used. The concentration of the aqueous solution of collagen is, for example, preferably from 1 ng/L to 50 mg/L, most preferably from 1 $\mu g/L$ to 10 mg/ml.

When the surface of the water-containing gel comprising alginic acid is coated with collagen intermediated by chitosan, both sides of the water-containing gel comprising alginic acid may be coated, or one side may be coated. In order to coat only one side, a coating method such as those mentioned above can be employed, or when a method based on immersion is employed, means of attaching a cover and the like can be employed so that the side will not contact with an immersion solution. When the surface of the water-containing gel comprising alginic acid is coated with collagen, total area of one surface or both surfaces may be coated, or a part of the total area may be coated with collagen. In addition, when the surface of the water-containing gel comprising alginic acid is coated with collagen intermediated by chitosan, the back surface or inside of the gel may be reinforced with fibers, mesh or the like to increase strength. Means for the reinforcement is not particularly limited. Examples include a method of retaining a nylon mesh in the gel and the like.

By using the carrier for cell culture of the present invention, cells can be cultured on its surface. Types of cells that can be cultured are not particularly limited. Examples thereof include, for example, fibroblasts, vascular endothelial cells, chondrocytes, hepatocytes, small intestine epithelial cells, epidermal keratinocytes, osteoblasts, bone marrow mesenchymal cells, embryonic stem cells, somatic stem cells and the like. For the cell culture, a culture medium (for example, D-MEM medium, MEM medium, HamF12 medium, or HamF10 medium) containing cells at a density of from 10,000 to 15,000 cells/ml is usually added onto the surface of the carrier for cell culture. The cell culture conditions can be appropriately chosen depending on the type of cells to be cultured. In general, the culture may preferably be continued until a confluent cell monolayer is formed on the carrier surface.

By using the carrier for cell culture according to the first embodiment of the present invention, multiple kinds of cells can be co-cultured on the carrier surface as plate culture. For example, cells that can grow only on cell-adhesive polypeptide such as fibroblasts and hepatocytes are cultured to form a monolayer of the cells on the polypeptide-modified portions on the carrier surface, and then cells such as vascular endothelial cells, that adhere to the anionic polysaccharide which coats the surfaces other than the polypeptide-modified portions, can be cultured to prepare cell culture containing two kinds of cells.

Culture of cells using the carrier for cell culture of the present invention can be performed specifically as follows. The carrier for cell culture is placed inside a petri dish or the like, then an appropriate culture medium (for example, D-MEM medium, MEM medium, HamF12 medium, HamF10 medium) is added to the petri dish to immerse the carrier for 5 minutes, and then the medium is exchanged. After this procedure is repeated three times, the culture system was left for 12 to 24 hours so that the culture medium can infiltrate into the carrier for cell culture. Then, the culture medium in the petri dish is discarded, and then cells are inoculated onto the gel layer of the carrier for cell culture, and further an appropriate culture medium (for example, D-MEM medium, MEM medium, HamF12 medium, HamF10 medium) is added to the petri dish. After the system is left at 37° C. for 1 to 2 hours so that the cells can be held by (adhered to) the carrier surface, the culture is continued at 37° C. During the culture, the culture medium may be exchanged, if needed. Usually, the culture medium is exchanged every 0.5 to 2 days of the culture. However, the method for cell culture is not limited to the aforementioned specific method, and it can be understood that an appropriate method can be chosen by those skilled in the art.

Cell culture obtained by culturing cells using the carrier for cell culture of the present invention contains the carrier for cell culture of the present invention and a cell array consisting of a cell layer retained on the carrier surface. The cell array retained on the surface of the carrier for cell culture is, for example, a cell layer formed on a surface of collagen, which is a cell-adhesive polypeptide, and is a cell array containing a cell layer being a monolayer, for example.

Laminated culture may be performed by putting a separately prepared cell sheet on cell culture obtained by utilizing the carrier for cell culture of the present invention. When a vascular endothelial cell layer or hepatocyte layer is used as the cell layer to be laminated, a three-dimensional tissue structure of the liver can be constructed. This three-dimensional tissue structure can be applied to in vitro drug permeability test, and also to an alternative model for animal experiment or to organs for transplantation. The laminated cell layers can be cultured with culture conditions depending on the kinds of cells constituting the cell layers. For the culture, various mediums such as D-MEM medium, MEM medium, HamF12 medium, and HamF10 medium can be used. For example, when the cell culture obtained by using the carrier for cell culture of the present invention is plate co-culture, further laminations may enable construction of three-dimensional cell tissue.

When a water-containing gel comprising alginic acid is used as the carrier, the cultured cells can be delaminated as a cell sheet or cell array by solubilizing the alginic acid gel layer of the cell culture obtained as described above. The solubilizing treatment of the alginic acid gel layer can be carried out by removing cation components that constitute the alginic acid gel. When the cation species is a polyvalent metal ion, the treatment can be performed by, for example, addition of ions such as phosphate that form a complex or hardly soluble salt with the polyvalent metal cation, use of an aqueous solution of chelating agent, decrease of the polyvalent metal ions in the medium, or concealment of the polyvalent metal ions in the medium with a chelating agent or the like. Since a medium for cell culture usually contains a vast amount of phosphate ions, a method of immersing into a medium from which polyvalent metal ions are eliminated beforehand, or into a medium added with chelating agent in an amount of 90 mol % or more based on the total molar number of the polyvalent metal cations is preferably used from a viewpoint of reduction of invasion into cells. The concentration of the chelating agent may preferably be from 90 to 10,000 mol %, more preferably 90 to 1,000 mol %.

The type of the chelating agent is not particularly limited. Examples include, for example, ethylenediamine-di-orthohydroxyphenylacetic acid, diaminopropanetetraacetic acid, nitrilotriacetic acid, hydroxyethylethylenediaminetriacetic acid, dihydroxyethylglycine, ethylenediaminediacetic acid, ethylenediaminedipropionic acid, iminodiacetic acid, diethylenetriaminepentaacetic acid, hydroxyethyliminodiacetic acid, 1,3-diaminopropanoltetraacetic acid, triethylenetetraminehexaacetic acid, trans-cyclohexanediaminetetraacetic acid, ethylenediaminetetraacetic acid (EDTA), glycol etherdiaminetetraacetic acid, O,O'-bis(2-aminoethyl)ethylene glycol-N,N,N',N'-tetraacetic acid (EGTA), ethylenediaminetetrakismethylenephosphonic acid, diethylenetriaminepentamethylenephosphonic acid, nitrilotrimethylenephosphonic acid, 1-hydroxyethylidene-1,1-diphosphonic acid, 1,1-diphosphonoethane-2-carboxylic acid, 2-phosphonobutane-1,2,4-tricarboxylic acid, 1-hydroxy-1-phosphonopropane-1,3,3-tricarboxylic acid, catechol-3,5-disulfonic acid, sodium pyrophosphate, sodium tetrapolyphosphate and sodium hexametaphosphate. Particularly preferred examples are diethylenetriaminepentaacetic acid, triethylenetetraminehexaacetic acid, 1,3-diaminopropanoltetraacetic acid, glycol etherdiaminetetraacetic acid, hydroxyethylethylenediaminetriacetic acid, 2-phosphonobutane-1,2,4-tricarboxylic acid, 1,1-diphosphonoethane-2-carboxylic acid, nitrilotrimethylenephosphonic acid, ethylenediaminetetraphosphonic acid, diethylenetriaminepentaphosphonic acid, 1-hydroxypropylidene-1,1-diphosphonic acid, 1-aminoethylidene-1,1-diphosphonic acid, 1-hydroxyethylidene-1,1-diphosphonic acid and salts thereof. Among them, particularly preferred are EDTA and EGTA.

The solubilization treatment of the alginic acid gel layer using a chelating agent is preferably carried out by infiltrating a chelating agent from the porous membrane on which surface an aqueous gel containing alginic acid is formed. By such operation, the porous membrane and the alginic acid gel layer can be easily separated, and the cell culture can be easily delaminated from the porous membrane. It is not necessary to completely delaminate the alginic acid gel layer by the solubilization treatment of the alginic acid gel layer, and the alginic acid gel layer remained unsolubilized may be left on the cell culture. However, the alginic acid gel layer is preferably solubilized and removed as much as possible.

The cell culture obtained by subjecting the alginic acid gel layer to the solubilization treatment contains a cell layer or cell array, and accordingly, the cell culture can be used for lamination, transfer or the like of cell layers. For lamination of a cell layer, the cells can be cultured on cells cultured beforehand with weighting, and then the alginic acid gel layer may be solubilized, or cell cultures obtained by solubilizing the alginic acid gel layers may be laminated. Further, cell culture obtained by solubilizing the alginic acid gel layer may be laminated on a cell layer separately prepared. Kinds of cells of the cell layers to be laminated may be the same or different. The number of the cell layers to be laminated is not particularly limited. Generally, the number is from 1 to 10, preferably from 1 to 5, more preferably from 1 to 3. For transfer of a cell layer, the cell layer may be cultured on another substrate for cell culture with weighting and then the alginic acid gel may be solubilized, or cell culture obtained by solubilizing the alginic acid layer may be transferred to another medium. Examples of preferred method for the lamination or the transfer include a method of carrying out culture with weighting on cells cultured beforehand or on another substrate for cell culture, and then dissolving the alginic acid gel.

The method for cell culture with weighting is not particularly limited, and the culture may be carried our by any method so long as sufficient weight is applied so that unevenness should not be formed in cells or substrate on which cells are transferred. If cells are sealed by weighting, cells may be smothered. Therefore, at least either of the cell culture substrates to be transferred or that to receive the transfer preferably consists of a water-permeable gel, porous membrane, or a combination thereof. Further, for uniform transfer, a weight should be applied so as to sufficiently cover the surface of the cell layer. However, uniform contact may disturb diffusion of oxygen, and therefore, a weight may preferably be applied through non-woven fabric (nylon, polyester, stainless steel and the like) or the like so as not to disturb diffusion of oxygen.

In the cell culture method with weighting, the weight to be applied is preferably from about 0.1 to 50 g/cm$^2$, more preferably from about 0.50 to 10 g/cm$^2$. The culture time of the cells under weighing is not particularly limited, and can be appropriately chosen so that sufficient transfer of cells can be achieved. The period of time is preferably 4 to 72 hours, more preferably from 6 to 48 hours.

The carrier for cell culture of the present invention may be sterilized by any method. Sterilization by radiation such as electron beam, γ-ray, X-ray, and ultraviolet ray may preferably be used. An electron beam, γ-ray, and ultraviolet ray are more preferably used, and electron beam sterilization is particularly preferred. An exposure dose for the electron beam sterilization according to the present invention is preferably from 0.1 to 65 kGy, most preferably from 1 to 40 kGy. Chemical sterilization such as ethylene oxide gas (EOG) sterilization and sterilization using a high temperature such as high pressure steamy gas sterilization may not be preferred, because the cell adhesion layer and the alginic acid gel layer may be decomposed. A carrier for cell culture sterilized as described above can be stored at room temperature for a long period of time, if it is stored under a sterile condition. The aforementioned sterilization methods may be used each alone or in combination. The same sterilization method may be applied repeatedly.

EXAMPLES

The present invention will be more specifically explained by referring to the following examples. However the scope of the present invention is not limited to these examples.

Example 1

Preparation of Carrier for Cell Culture (1) Preparation of Water-containing Alginic Acid Gel Membrane An aqueous solution containing 5 weight % of sodium alginate (produced by Wako Pure Chemical Industries) was applied on a stainless steel substrate with a thickness of 500 μm, and the coated substrate was immersed in a 0.5 mol/l solution of calcium chloride in water and methanol (volume ratio=80:20). After the applied solution sufficiently gelled, the coated substrate was washed with running water. Further, the coated substrate was dried, in a state that its four sides were pinched to prevent deformation of the membrane, to obtain a water-containing calcium alginate gel membrane.

(2) Modification with Chitosan

The water-containing alginic acid gel membrane obtained in the above (1) was immersed in a 1 weight % aqueous solution of water-soluble chitosan (produced by Wako Pure Chemical Industries) for 1 hour and washed with running water for 1 hour or more. The chitosan-modified membrane was not dried and stored in water.

(3) Modification with Collagen

Cellmatrix I-C (aqueous solution of type I collagen produced by Nitta Gelatin) diluted with water to 0.03 mg/ml was spotted on the chitosan-modified membrane obtained in the above (2) with a stainless steel pin having a tip bow pen shape, and then the substrate was washed with running water for 1 hour or more. Further, the coated substrate was dried, in a state that its four sides were pinched to prevent deformation of the membrane, to obtain a water-containing calcium alginate gel membrane of which surface was modified with collagen in a sea-island structure (Sample 1). The method of the spotting in the above procedure is shown in FIG. 1. Further, spots were also formed by spotting with a capillary (MICROCAPS produced by Drummmond Scientific, volume: 5 μl) to obtain Sample 2.

(4) Modification with Hyaluronic Acid

Samples 1 and 2 were immersed in a 0.1% aqueous solution of sodium hyaluronate (produced by Wako Pure Chemical Industries, produced from chicken crest) for 1 hour and washed with running water for 1 hour or more. Further, the coated samples were dried, in a state that four sides of each were pinched to prevent deformation of the membranes, to obtain Samples 3 and 4 (water-containing calcium alginate gel membranes of which surfaces are modified with collagen in a sea-island structure and in which portions other than the collagen-modified portions were coated with hyaluronic acid).

(5) Evaluation of Collagen-adhered Portions (i) Immunostaining

Figure 2:
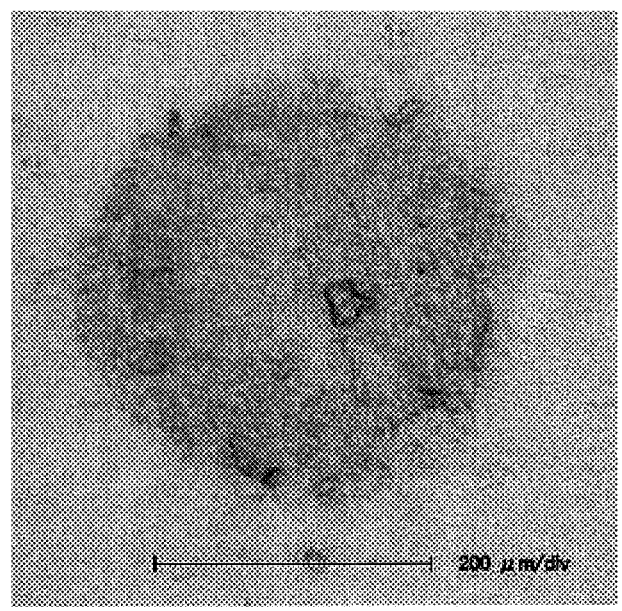
FIG. 2 shows results of immunostaining of collagen-modified portions formed on a carrier surface in a sea-island structure.

For the samples obtained above, the membranes were washed with PBS+ (obtained by mixing 100 ml of 10× Dulbecco's phosphate-buffered saline produced by GIBCO, without calcium chloride, without magnesium chloride, with 899 ml of water and 1 ml of aqueous solution containing 100 g/l of magnesium chloride hexahydrate and 100 g/l of calcium chloride), and the samples were immersed in TBS Blotto B solution prepared according to a manual at room temperature for 2 hours. After the TBS Blotto B solution was sufficiently removed, the samples were applied with anti-type-I collagen rabbit antibodies (produced by Santa Cruz Biotechnology) as primary antibodies, left for 1 hour and then washed with PBS+. Subsequently, the samples were applied with anti-rabbit antibodies labeled with peroxidase (Envision+™ Peroxidase produced by DAKO) as secondary antibodies, left for 1 hour and washed with PBS+. After the washing solution was sufficiently removed, the samples were reacted with a DAB substrate solution (prepared according to the manual of Liquid DAB+ Substrate-Cromogen System produced by DAKO) for 2 minutes under ice cooling. It was observed that collagen-adhered portions were formed in a sea-island structure in all of Samples 1 to 4. One independent collagen-adhered portion had an area of 0.05 mm$^2$ in Samples 1 and 3, or 0.8 mm$^2$ in Samples 2 and 4. The result of staining of Sample 3 is shown in FIG. 2.

(ii) XPS

Compounds in the uppermost layers of the samples obtained above were evaluated by analyzing chemical shifts of 1 s orbits of N atom, C atom, and O atom on the surfaces of the samples using XPS. As a result, it was found that the collagen-spotted portion of Samples 1 to 4 consisted of collagen, and that portions other than the collagen-spotted portions consisted of chitosan in Samples 1 and 2 or hyaluronic acid in Samples 3 and 4.

(6) Sterilization

After the carriers obtained above were subjected to UV sterilization for 3 hours and electron beam sterilization at 20 kGy, no bacterium was found in each of the carriers. In the samples not subjected to any sterilization treatment, 5,900 cells/m$^2$ of bacteria were observed.

Comparative Example 1

The procedures of Example 1 up to the modification with collagen were performed by using polyethylene terephthalate (PET) or glass instead of the water-containing alginic acid gel. As a result, no adhesion of collagen was observed.

Example 2

Modification of Glass

Glass, used as a carrier, was immersed in a 10 weight % aqueous solution of 3-aminopropyltriethoxysilane (produced by Wako Pure Chemical Industries), left at 50° C. for 2 hours and then washed with running water for 1 hour to prepare glass introduced with amino groups. The procedures of Example 1 up to the modification with collagen were performed by using this glass introduced with amino groups instead of the water-containing alginic acid gel. As a result, adhesion of collagen was observed.

Example 3

Culture of Cells

Cells were cultured by using the carriers for cell culture as follows.

(1) Used Cell

CHL (Chinese Hamster Lung Cell)

(2) Used Medium

Eagle's minimum medium containing 10% fetal bovine serum (3) Carrier for Cell Culture Samples 3 and 4 prepared in Example 1, and a carrier for cell culture adhered to the bottom surface of a polystyrene cell culture dish with double-sided tapes were subjected to UV sterilization and added with the medium for immersion for 5 minutes. The medium was exchanged three times, and then the carriers for cell culture were left overnight to allow the medium to infiltrate into the carriers. The same procedure was performed for polystyrene cell culture dish as a comparative example without any treatment.

(4) Inoculation of Cells

The cells cultured beforehand were collected by trypsin treatment, and the cell density was adjusted to 50,000 cells/ml. After the medium in the cells and dishes was discarded, the cell suspension was inoculated into the dishes at a cell number of 10,000 cells/cm$^2$, and then the medium was added.

(5) Culture

The cells were cultured at 37° C. for two days by using a $CO_2$ incubator.

(6) Results

No problem occurred for each of the samples as for cell adhesion, delamination of carrier for cell culture, and cytotoxicity. In Samples 3 and 4 prepared in Example 1, the cultured cells were found only on the collagen-adhered portions in a sea-island structure, and thus a cell array was formed.

Test Example 1

Evaluation of Adsorption to Calcium Alginate, Chitosan and Collagen

The water-containing calcium alginate gel, chitosan-modified water-containing calcium alginate gel, and collagen-modified gel prepared by immersing the chitosan-modified water-containing calcium alginate gel in CellmatrixIC (aqueous solution of type I collagen produced by Nitta gelatin) diluted with water to 0.03 mg/ml and washing the resulting gel with water, which were prepared in Example 1, were each immersed in each 0.1 weight % solution of collagen, chitosan, sodium hyaluronate, or sodium alginate, and then washed with water, and adsorption was evaluated by XPS. The results are shown in Table 1. All the evaluated polymer compounds were found to adhere to chitosan, whereas all the evaluated polymer compounds did not adhered to collagen.

TABLE 1

| | Na alginate | Chitosan | Collagen | Na hyaluronate |
|---|---|---|---|---|
| Water-containing calcium alginate gel | Not evaluated | Adhered | Adhered | Not adhered |
| Chitosan-modified water-containing calcium alginate gel | Adhered | Not evaluated | Adhered | Adhered |
| Collagen-modified water-containing calcium alginate gel | Not adhered | Not adhered | Not evaluated | Not adhered |

Example 4

Preparation of Carrier for Cell Culture (1) Preparation of Water-containing Alginic Acid Gel Membrane i) Water-containing Calcium Alginate Gel Membrane An aqueous solution containing 5 weight % of sodium alginate (produced by Wako Pure Chemical Industries) was applied on a stainless steel substrate with a thickness of 500 μm, and the coated substrate was immersed in a 0.5 mol/l solution of calcium chloride in water and methanol (volume ratio=80:20). After the applied solution sufficiently gelled, the coated substrate was washed with running water. Further, the coated substrate was dried, in a state that its four sides were pinched to prevent deformation of the membrane, to obtain a water-containing calcium alginate gel membrane.

ii) Water-containing Alginic Acid/Polylysine Gel Membrane (Nylon Mesh-Reinforced Type)

An aqueous solution containing 2 weight % of sodium alginate, 3.2 weight % of 1-ethyl-3-(3-dimethylaminopropyl)carbodiimide hydrochloride (WSC, produced by Peptide Institute), 0.68 weight % of N-hydroxysuccinimide (NHS, produced by Peptide Institute) and 0.6 weight % of lysine (produced by Wako Pure Chemical Industries) was applied on a stainless steel substrate with a thickness of 200 ml/m$^2$, and a nylon net filter NY1H produced by Millipore was sunk in the solution. Then, the same solution was coated on the stainless steel substrate with a thickness of 1000 ml/m$^2$. Subsequently, the substrate was immersed in a 0.1 M aqueous solution of calcium chloride for 1 hour to obtain a water-containing alginic acid/polylysine membrane. The water-containing alginic acid/polylysine membrane was not dried and stored in water.

2) Modification with Chitosan

The water-containing alginic acid gel membrane obtained in the above (1) was immersed in a 1 weight % aqueous solution of water-soluble chitosan (produced by Wako Pure Chemical Industries) for 1 hour and washed with running water for 1 hour or more. The chitosan-modified membrane was not dried and stored in water.

3) Coating with Collagen

The chitosan-modified membrane obtained in the above (2) was immersed in Cellmatrix I-C (aqueous solution of type I collagen produced by Nitta Gelatin) diluted with water to 0.03 mg/ml for 1 hour and washed with running water for 1 hour or more. Further, the coated substrate was dried, in a state that its four sides were pinched to prevent deformation of the membrane, to obtain a water-containing calcium alginate gel membrane of which surface was coated with collagen.

4) Comparative Example

A water-containing alginic acid gel membrane without treatment using chitosan and collagen, and a water-containing alginic acid gel membrane modified only with chitosan were prepared as comparative examples.

5) Sterilization

The membranes obtained in Example 4 were subjected to UV sterilization for 3 hours and electron beam sterilization at 20 kGy. As a result, no bacterium was observed in each of the carriers. In the samples not subjected to any sterilization treatment, 7500 cells/m$^2$ of bacteria were confirmed.

Example 5

Culture of Cells Using Carrier for Cell Culture

Cells were cultured by using the carriers for cell culture as follows.

1) Used Cell

CHL (Chinese Hamster Lung Cell)

2) Used Medium

Eagle's minimum medium containing 10% fetal bovine serum

3) Carrier for Cell Culture

Each of the carriers for cell culture prepared in Example 1 was adhered to a frame, which was obtained by removing a collagen membrane from a permeable collagen membrane for cell culture, MEN-01, produced by KOKEN CO., LTD., and then put into a polystyrene cell culture dish. The carriers were added with the medium for immersion for 5 minutes, and then the medium was exchanged. This procedure was repeated three times, and then the carriers were left overnight to allow the medium to infiltrate into the carriers for cell culture. The same procedure was performed for the permeable collagen membrane for cell culture, MEN-01, produced by KOKEN CO., LTD as a comparative example. Combinations of the used carriers for cell culture and sterilization methods are shown in Table 2.

4) Inoculation of Cells

The cells cultured beforehand were collected by trypsin treatment, and the cell density was adjusted to 50,000 cells/ml. After the medium in the cells and dishes was discarded, the cell suspension was inoculated into the dishes at a cell number of 10,000 cells/cm$^2$, and then the medium was added.

5) Culture

The cells were cultured at 37° C. for two days by using a $CO_2$ incubator.

6) Evaluation

As deformation of the membranes, the height of the center portion protruding from the peripheral portions was evaluated after immersion in the medium for 1 day. A larger protrusion will make the observation under an optical microscope more difficult, and when the height is larger than 5 mm, the membrane will contact with the culture dish, which may result in insufficient supply of substances from the back surface. Cell adhesion and toxicity were evaluated by observing the cells under an optical microscope.

7) Results

Figure 3:
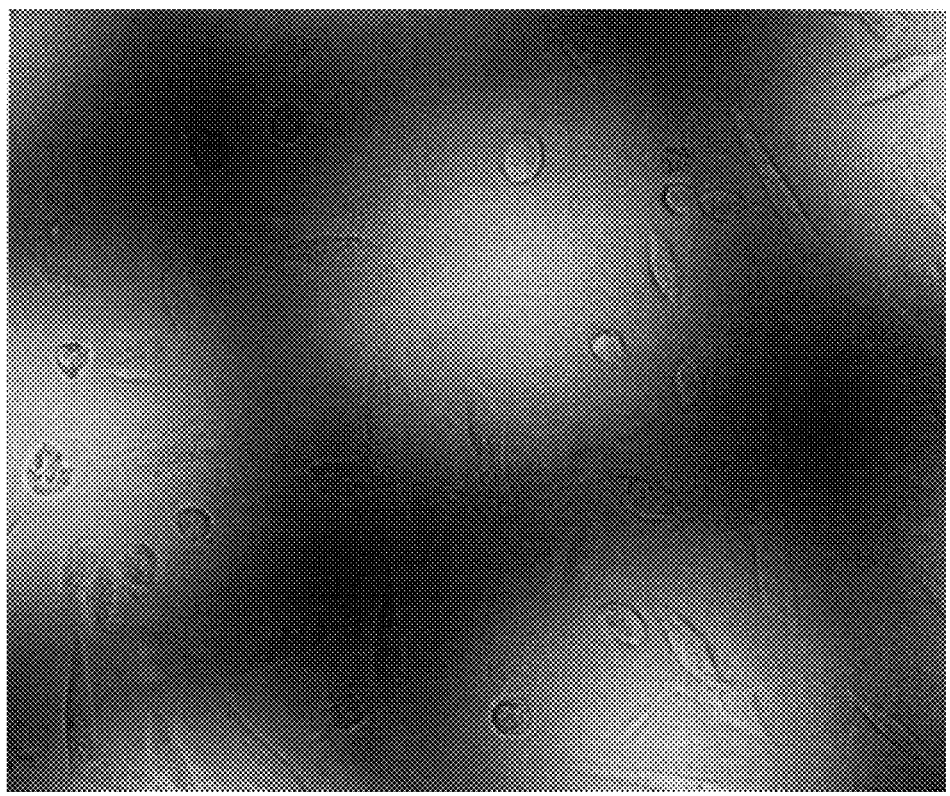
FIG. 3 is an optical microphotograph of cells cultured by using a water-containing alginic acid/polylysine gel membrane (nylon mesh-reinforced type) coated with collagen via chitosan.

The results are shown in Table 2. The carriers for cell culture of the present invention had no toxicity, and gave favorable cell adhesion and extremely small deformation of the membrane. An optical microphotograph of the cells cultured by using the collagen-coated water-containing alginic acid/polylysine gel membrane (nylon mesh-reinforced type) is shown in FIG. 3.

TABLE 2

| Sample | Water-containing alginic acid gel membrane | Modification with chitosan | Modification with collagen | Sterilization | Deformation (mm) | Observation of cells | Cell adhesion | Toxicity | |
|---|---|---|---|---|---|---|---|---|---|
| | | | | | Non-delamination solution | | | | |
| 101 | Calcium | Not used | Not used | UV | 2 | Δ | X | ○ | Comparative |
| 102 | " | Used | " | " | 1 | ⊙ | ○ | X | " |
| 103 | " | " | Used | " | 1 | ⊙ | ⊙ | ⊙ | Invention |
| 104 | " | " | " | Electron beam | 1 | ⊙ | ⊙ | ⊙ | " |
| 105 | Polylysine | Not used | Not used | UV | 0 | ○ | X | Δ | Comparative |
| 106 | " | Used | " | " | 0 | ○ | ○ | X | " |
| 107 | " | " | Used | " | 0 | ○ | ⊙ | ⊙ | Invention |
| 108 | MEN-01 | | | | 5> | X | ⊙ | ⊙ | Comparative |

<Evaluation criteria for observation of cells>
⊙: Cells can be sufficiently observed over the entire membrane.
○: Cells can be observed over substantially entire membrane
Δ: Cells in the center portion can be observed.
X: It is difficult to focus over the entire field of view.

<Evaluation criteria for cell adhesion>
⊙: 90% or more of cells adhere.
○: 70% or more of cells adhere.
Δ: 30% or more of cells adhere.
X: Adhering cells account for 10% or less.

<Evaluation criteria for toxicity>
⊙: 90% or more of cells survive
○: 70% or more of cells survive.
Δ: 30% or more of cells survive.
X: Surviving cells account for 10% or less.

Example 6

Study on Conditions for Preparation of Water-containing Calcium Alginate Gel Membrane An aqueous solution containing 5 weight % of sodium alginate (produced by Wako Pure Chemical Industries) was applied on a stainless steel substrate with a thickness of 500 μm, and the coated substrate was immersed in each solution mentioned in Table 3. After the applied solution sufficiently gelled, the coated substrate was washed with running water. The water-containing alginic acid gel membrane obtained as described above was immersed in a 1 weight % aqueous solution of water-soluble chitosan (produced by Wako Pure Chemical Industries) for 1 hour and washed with running water for 1 hour or more. Then, the chitosan-modified membrane was immersed for 1 hour in Cellmatrix I-C (aqueous solution of type I collagen produced by Nitta Gelatin), which was diluted with water to 0.03 mg/ml, and then washed with running water for 1 hour or more. Further, the coated substrate was dried, in a state that its four sides were pinched to prevent deformation of the membrane, to obtain a water-containing calcium alginate gel membrane of which surface was coated with collagen. Membrane strength of the water-containing calcium alginate gel membrane, of which surface was coated with collagen obtained as described above, was examined in the medium by tactile impression. The results are shown in Table 3. The carriers for cell culture of the present invention had favorable strength.

TABLE 3

| Sample | Calcium chloride concentration (mol/l) | Solvent (volume ratio) | | Membrane strength | |
|---|---|---|---|---|---|
| 201 | 0 | Water | X | Membrane could not be obtained due to dissolution during washing with water. | Comparative |
| 202 | 0.5 | " | Δ | Membrane had strength, but was slightly brittle. | Invention |
| 203 | " | Water/methanol (90/10) | ⊙ | Membrane also had flexibility, and handling was easy | " |
| 204 | 0 | Water/methanol (80/20) | X | Membrane could not be obtained due to dissolution during washing with water. | Comparative |
| 205 | 0.1 | Water/methanol (80/20) | ⊙ | Membrane also had flexibility, and handling was easy | Invention |
| 206 | 0.5 | Water/methanol (80/20) | ⊙ | Membrane also had flexibility, and handling was easy | " |
| 207 | 1.0 | Water/methanol (80/20) | ⊙ | Membrane also had flexibility, and handling was easy | " |

TABLE 3-continued

| Sample | Calcium chloride concentration (mol/l) | Solvent (volume ratio) | Membrane strength | |
|---|---|---|---|---|
| 208 | 0.5 | Water/methanol (50/50) | ◎ Membrane also had flexibility, and handling was easy | " |
| 209 | 0 | Methanol | X Membrane was dissolved with medium. | Comparative |
| 210 | 0.2 | " | ○ Membrane had sufficient strength. | Invention |
| 211 | 0.1 | Water/ethanol (85/15) | ○ Membrane had sufficient strength. | " |

INDUSTRIAL APPLICABILITY

By culturing cells using the carrier for cell culture of the present invention, a cell array can be easily formed. Further, the carrier for cell culture of the present invention is free from deformation due to swelling in a medium and the like, and thus the carrier enables easy observation of cultured cells under an optical microscope.

What is claimed is:

1. A carrier for cell culture in the form of a sheet comprising a water-containing gel layer, which comprises alginic acid or alginate and an intermediate layer of chitosan, wherein the intermediate layer of chitosan binds the alginic acid or alginate gel layer to a collagen layer, wherein the chitosan is formed from a 1-5% aqueous solution.

2. The carrier for cell culture according to claim 1, wherein the water-containing gel contains calcium alginate gel or alginic acid/polylysine gel.

3. The carrier for cell culture according to claim 1, wherein the water-containing gel is formed on a porous membrane.

4. A method for producing the carrier for cell culture according to claim 1, which comprises the step of successively immersing the water-containing gel in the chitosan solution and then in a collagen solution.

5. A method for culturing cells, which comprises the step of allowing cells to form a cell layer on the carrier for cell culture according to claim 1.

6. A cell culture obtained by the method according to claim 5 comprising said carrier for cell culture and said cell layer.

7. A method for producing a cell culture, which comprises a step of allowing cells to form a cell layer on a surface of the carrier for cell culture according to claim 1 and a step of solubilizing the water-containing gel comprising alginic acid or alginate.

* * * * *

UNITED STATES PATENT AND TRADEMARK OFFICE
CERTIFICATE OF CORRECTION

PATENT NO.        : 7,267,982 B2                                          Page 1 of 1
APPLICATION NO.   : 10/612955
DATED             : September 11, 2007
INVENTOR(S)       : Hirohiko Tsuzuki It is certified that error appears in the above-identified patent and that said Letters Patent is hereby corrected as shown below:

Title Page, item [30] should read as follows:
Foreign Application Priority Data

Jul 05, 2002 [JP]  2̶0̶0̶0̶-̶1̶9̶6̶7̶2̶5̶ 2002-196725

Jul 05, 2002 [JP]  2̶0̶0̶0̶-̶1̶9̶6̶7̶2̶6̶ 2002-196726

Signed and Sealed this

First Day of April, 2008

JON W. DUDAS
*Director of the United States Patent and Trademark Office*